;; (12) United States Patent
Osawa et al.

(10) Patent No.: US 7,872,798 B2
(45) Date of Patent: Jan. 18, 2011

(54) MICROSCOPIC APPARATUS AND OBSERVING METHOD

(75) Inventors: Hisao Osawa, Kashiwa (JP); Yumiko Ouchi, Tokyo (JP)

(73) Assignee: Nikon Corporation, Tokyo (JP)

( * ) Notice: Subject to any disclaimer, the term of this patent is extended or adjusted under 35 U.S.C. 154(b) by 661 days.

(21) Appl. No.: 11/886,124

(22) PCT Filed: Sep. 22, 2006

(86) PCT No.: PCT/JP2006/318874

§ 371 (c)(1),
(2), (4) Date: Sep. 11, 2007

(87) PCT Pub. No.: WO2007/043313

PCT Pub. Date: Apr. 19, 2007

(65) Prior Publication Data

US 2008/0192337 A1     Aug. 14, 2008

(30) Foreign Application Priority Data

Oct. 11, 2005    (JP)    ............................. 2005-296815

(51) Int. Cl.
*G02B 23/00* (2006.01)
*H01J 3/14* (2006.01)
(52) U.S. Cl. ........................ 359/385; 359/368; 250/234
(58) Field of Classification Search .......... 359/368–390
See application file for complete search history.

(56) References Cited

U.S. PATENT DOCUMENTS

| 6,239,909 | B1 | 5/2001 | Hayashi et al. | |
| 2003/0132394 | A1 | 7/2003 | Wolleschensky et al. | |
| 2004/0113059 | A1 | 6/2004 | Kawano et al. | |
| 2008/0158668 | A1* | 7/2008 | Ouchi et al. | 359/385 |
| 2009/0268280 | A1* | 10/2009 | Osawa et al. | 359/363 |

FOREIGN PATENT DOCUMENTS

| JP | A 11-242189 | 9/1999 |
| JP | A 2002-323660 | 11/2002 |
| JP | A 2004-199063 | 7/2004 |

* cited by examiner

*Primary Examiner*—Thong Nguyen
(74) *Attorney, Agent, or Firm*—Oliff & Berridge, PLC

(57) ABSTRACT

A microscopic apparatus and an observing method can obtain information of a super-resolved image of an object under observation with a high SN ratio. Therefore, the microscopic apparatus including an illuminating optical system that illuminates a specimen plane of a sample with line-shaped illuminating light, a modulating unit that spatially modulates the illuminating light in a lengthwise direction, an image-forming optical system that forms an image of light from the specimen plane illuminated with the spatially modulated illuminating light, and a detector that detects light from the specimen plane. Accordingly, a confocal effect is obtained with respect to an unstructuring direction of an illuminated area. The essential contrast of the structured illumination of the illuminated area is enhanced by the confocal effect, and thus the modulated image of the illuminated area is detected with a high SN ratio.

8 Claims, 5 Drawing Sheets

[Fig.1]
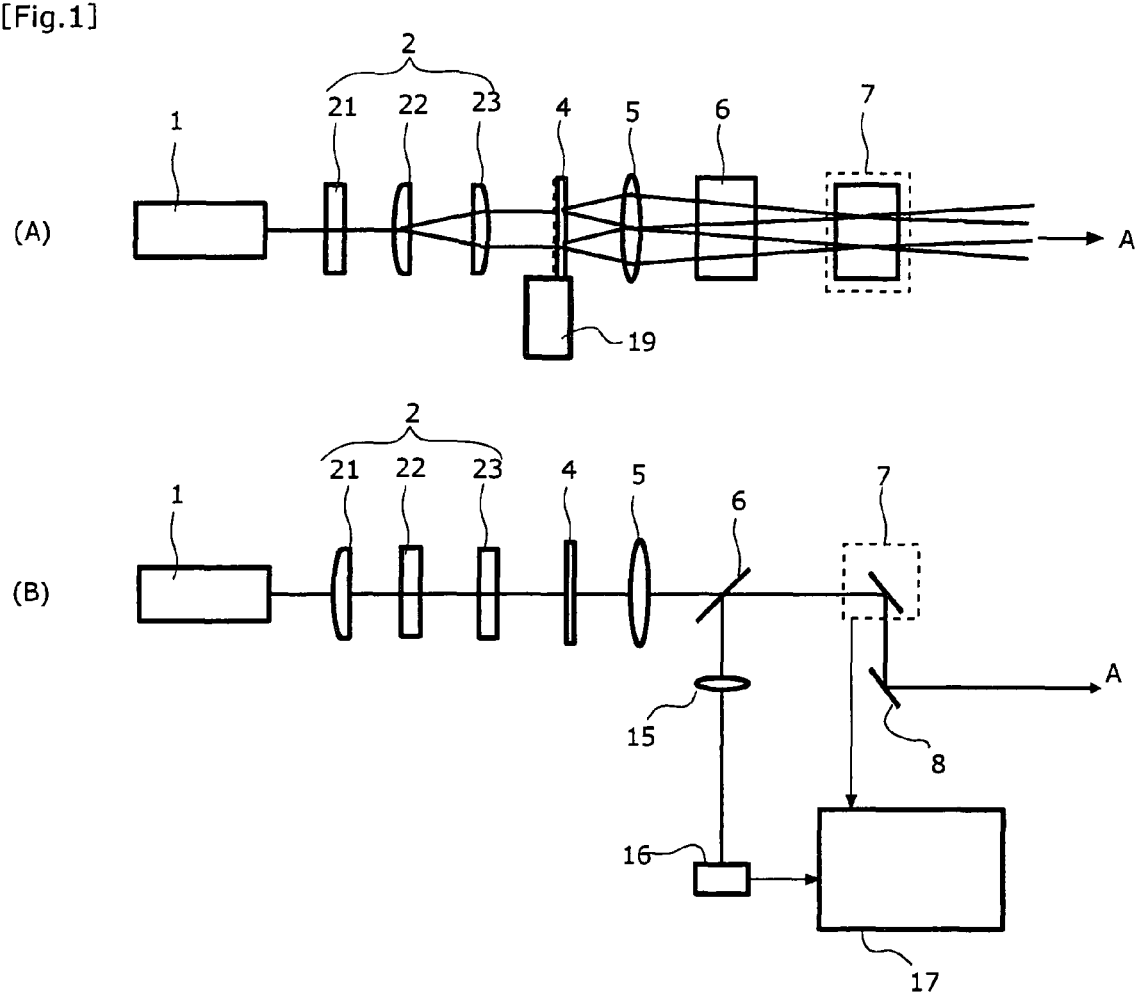
[Fig.2]
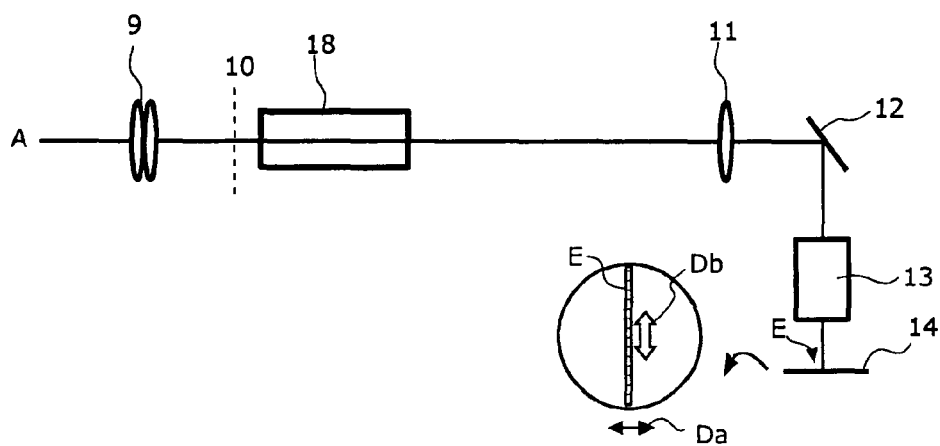

[Fig.3]
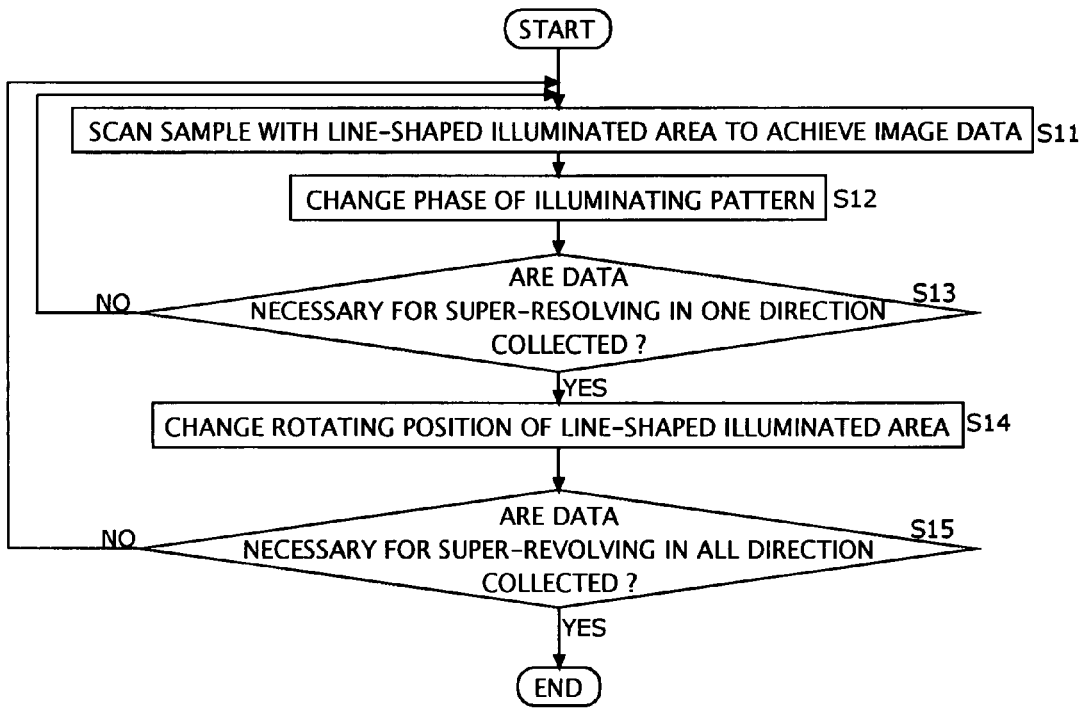
[Fig.4]
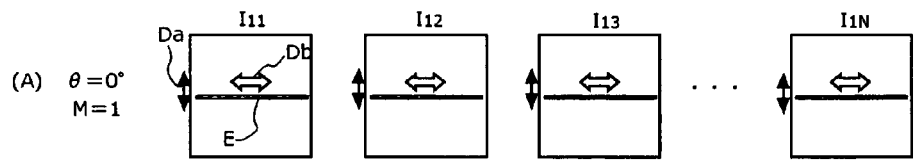
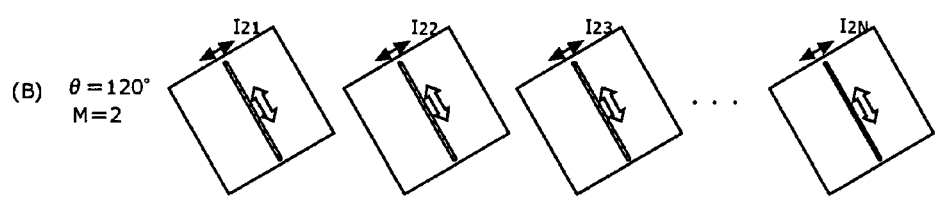
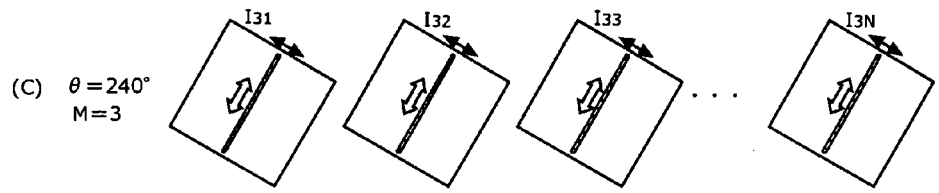
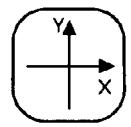

[Fig.5]
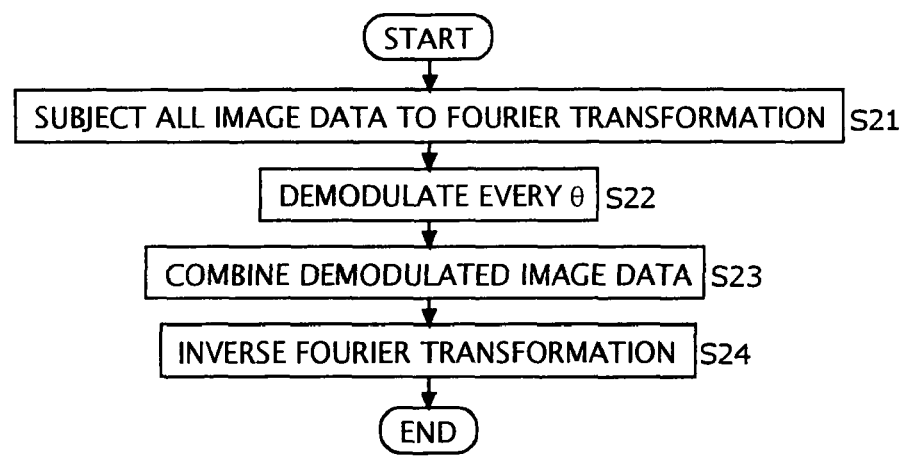

[Fig.6]
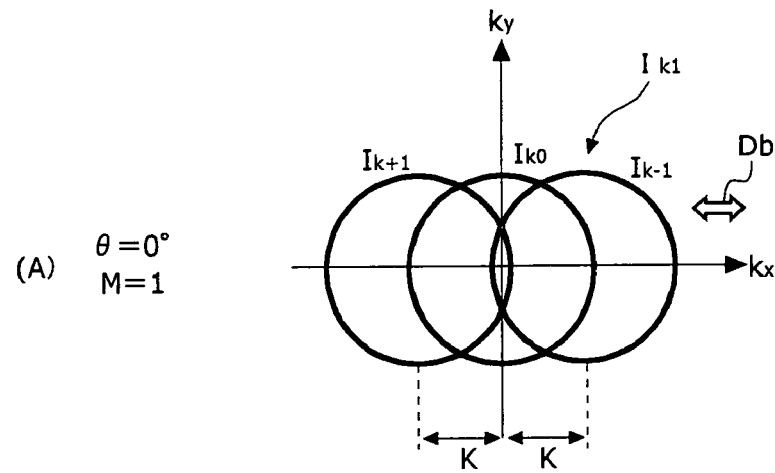
(A) θ=0°, M=1
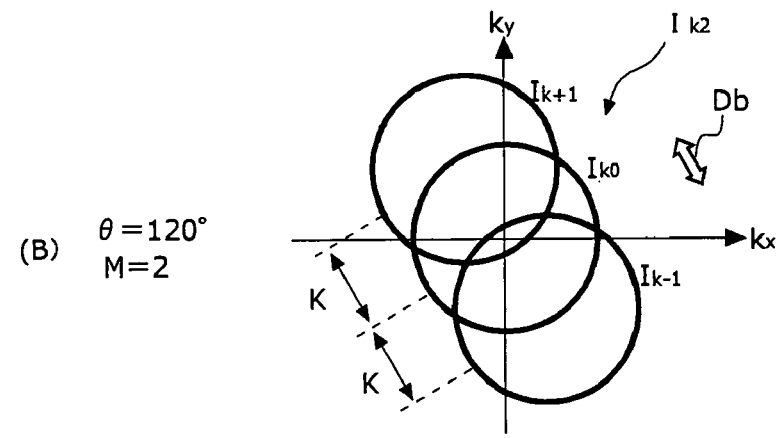
(B) θ=120°, M=2
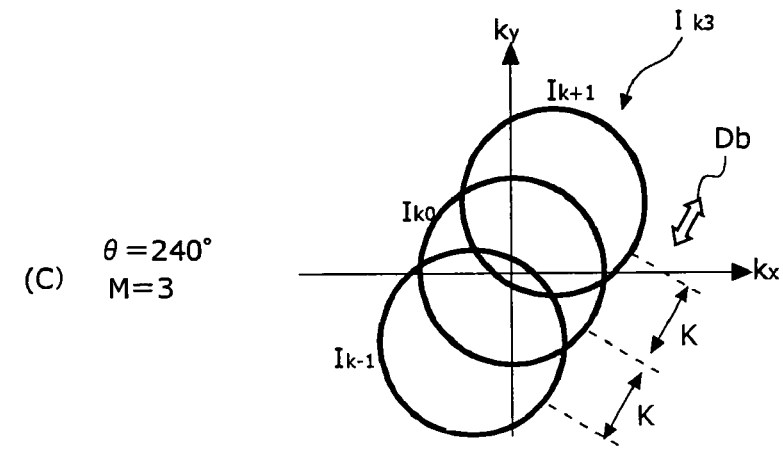
(C) θ=240°, M=3

[Fig.7]
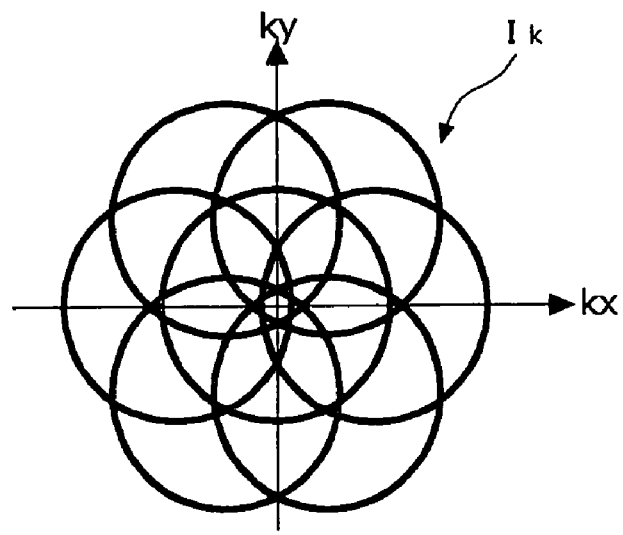

MICROSCOPIC APPARATUS AND OBSERVING METHOD

CROSS-REFERENCE TO RELATED APPLICATION

This application is a U.S. National Stage application claiming the benefit of prior filed International Application Number PCT/JP2006/318874, filed Sep. 22, 2006, in which the International Application claims a priority date of Oct. 11, 2005 based on prior filed Japanese Application Number 2005-296815 the entire contents of which are incorporated herein by reference.

TECHNICAL FIELD

The present invention relates to a microscopic apparatus and an observing method.

BACKGROUND ART

Recently, a super-resolution technology for observing a sample with a higher solution than the resolution of a microscopic optical system has been proposed (Patent Document 1, etc.). The Patent Document 1 discloses a structured illuminating method for exposing a sample to structured-illumination to generate a modulated image, detecting a modulated image at plural times with an image sensor while changing the phase of the structured-illumination, and demodulating these modulated images by a calculation, thereby obtaining a super-resolved image.

A recess portion called as a missing cone exists in the neighborhood of the zero spatial frequency of a transfer function of a normal microscopic optical system. Therefore, with respect to a pattern having low spatial frequencies contained in the sample, it is impossible to decompose the pattern in the optical axis direction and observe the pattern concerned. However, according to the structured illuminating method, the transfer function is substantially enlarged (the transfer function concerned corresponds to that obtained by displacing the transfer function of the microscopic optical system by only the spatial frequency of the structure illumination and superposing thus obtained transfer functions), and thus if the spatial frequency of the structured illumination is merely properly set, it would be expected that the missing cone is eliminated and high-resolution observation in the optical axis direction can be performed.

Patent Document 1: Japanese Unexamined Patent Application Publication No. Hei11-242189

DISCLOSURE

Problems to be Solved

However, this structured illuminating method has the following problem.

In general, a microscopic optical system requiring super-resolution uses an objective lens having a high numerical aperture, and the focal depth is shallower than the numerical aperture. At this time, many light beams from portions other than a specimen plane of the sample are incident to an image sensor, and thus the contrast of the structured illumination is reduced as a matter of practice.

In the structured illuminating method, it is more difficult to obtain a super-resolved image as the contrast of the structured illumination is lower. The reason for this is as follows. If the contrast of the structure illumination is low, the intensities of ±1 st-order modulated components contained in a modulated image are lower than the intensities of a 0th-order modulated component, however, the intensity of noise superposed on the modulated image is dominated by the 0th-order modulated component having the higher intensity, so that the ±1st-order modulated components which are important to the super-resolved image are embedded in the noise.

Therefore, the present invention has an object to provide a microscopic apparatus and an observing method with which information of a super-resolved image of an object under observation can be obtained at a high SN ratio.

SUMMARY

A microscopic apparatus of the present invention is characterized by including: an illuminating optical system that illuminates a specimen plane of a sample with a line-shaped illuminating light; a modulating unit that spatially modulates the illuminating light in a lengthwise direction; an image-forming optical system that forms an image of light from the specimen plane illuminated with the spatially modulated illumination light; and a detector for detecting the light from the specimen plane.

It is preferable that the microscopic apparatus of the present invention is further equipped with a mechanism for rotating the illumination light relatively to the specimen plane.

Furthermore, it is preferable that the microscopic apparatus of the present invention is further equipped with a mechanism for scanning the specimen plane with the illumination light.

It is also preferable that the microscopic apparatus of the present invention is further equipped with a mechanism of changing the phase of the spatial modulation.

Furthermore, it is preferable that the microscopic apparatus of the present invention is further equipped with a control unit for obtaining data of a brightness distribution at plural times while the mechanism is driven.

Furthermore, an observing method of the present invention is characterized by having: a step that illuminates a specimen plane of a sample with a line-shaped illuminating light; a step that spatially modulating the illumination light in a lengthwise direction; a step that forms an image of light from the specimen plane illuminated with the spatially modulated illumination light; and a step that detects light from the specimen plane.

EFFECT

According to the present invention, there is implemented a microscopic apparatus and an observing method that can obtain information of a super-resolved image of an object under observation with a high SN ratio.

BRIEF DESCRIPTION OF THE DRAWINGS

FIG. 1 is a diagram showing an optical system portion of a microscopic apparatus according to an embodiment;

FIG. 2 is a diagram showing the optical system subsequent to A of FIG. 1;

FIG. 3 is a flowchart showing an operation associated with the control of a data-processing unit 17;

FIG. 4 is a diagram showing image data of obtained modulated images of 3N;

FIG. 5 is a flowchart showing an operation associated with the calculation of the data-processing unit 17;

FIG. 6 is a diagram showing the processing of a step S22; and

FIG. 7 is a diagram showing the processing of a step S23.

DETAILED DESCRIPTION OF THE EMBODIMENTS

An embodiment of the present invention will be described hereunder. This embodiment corresponds to an embodiment of a microscopic apparatus.

First, the construction of the microscopic apparatus will be described.

FIGS. 1 and 2 are diagrams showing the construction of an optical system portion of the microscopic apparatus. FIGS. 1(A), (B) show an optical path of the microscopic apparatus when viewed from sides which are angularly different by 90°. FIG. 2 shows an optical path subsequent to a place indicated by a symbol A in FIGS. 1(A), (B).

As shown in FIGS. 1, 2, in the microscopic apparatus are arranged a light source 1 such as a laser light source or the like, a beam-shaping lens 2, a grating 4, an actuator 19, a collimating lens 5, a dichroic mirror 6, a scanning unit 7, a reflecting mirror 8, a collecting lens 15, a one-dimensional light detector (line sensor) 16, a data-processing unit 17 including a computer, circuits, etc., a scanner lens 9, an image rotator 18, a secondary objective lens 11, a reflecting mirror 12, an objective lens 13, a sample 14 marked with fluorescent material, an image-displaying unit (not shown), etc. The reflecting mirrors 8, 12, etc. are required in consideration of the arrangement of the optical path, and thus they are not indispensable. Furthermore, an exciting filter, a barrier filter, etc. may be arranged in an incident optical path or an emission optical path of the dichroic mirror 6.

Light emitted form the light source 1 is shaped to parallel light having a line-shaped cross-section (parallel light extending in one-dimensional direction) by three cylindrical lenses 21, 22, 23 of the beam-shaping lens 2. The longitudinal direction of the cross-section is desired to have the length corresponding to at least the width of the visual field of the objective lens 13.

This parallel light is incident to the grating 4 disposed at a position which is optically conjugated with the sample 14, so that diffracted components of respective orders are generated. The diffraction direction corresponds to the longitudinal direction of the parallel light.

The grating 4 is a phase type or amplitude type one-dimensional grating (a transmission type grating in the figures), for example. Particularly, the phase type is preferable because it hardly generates 0th-order diffracted component. However, under the present circumstances, some 0th-order diffracted component leaks out, and thus it is preferable that a masking member for masking the 0th-order diffracted component is disposed at the pupil position so that the 0th-order diffracted component does not reach the sample 14 (0th-order masking). The 0th-order masking is also required when the amplitude type grating is used. For the 0th-order masking, an absorption film may be formed at the center of the scanning unit 7 disposed at the pupil position. However, it is preferable that a relay optical system is disposed between the grating 4 and the collimating lens 5, and also the masking member is disposed at the pupil position in the relay optical system. Furthermore, the grating 4 is movable in a direction perpendicular to the grid lines by the actuator 19.

±1st-order diffracted components occurring in the grating 4 are incident to the dichroic mirror 6 through the collimating lens 5, and passed through the dichroic mirror 6. These ±1st-order diffracted components form a spatial image (line-shaped spatial image) of the grating 4 on a 1st-order image plane 10 through the scanning unit 7, the reflecting mirror 8 and the scanner lens 9. This spatial image is projected onto the sample 14 through the image rotator 18, the secondary objective lens 11, the reflecting mirror 12 and the objective lens 13. Accordingly, the sample 14 is illuminated (structured illumination) with line-shaped illuminating light whose intensity is spatially modulated in a sinusoidal shape in the longitudinal direction thereof. The focal plane of the objective lens 13 is coincident with the specimen plane in the sample 14. When attention is paid to only this specimen plane, the contrast of the structure illumination is high. However, when attention is further paid to the upper and lower layers of the specimen plane, the contrast of the structure illumination is low.

Fluorescence occurs in a line-shaped illuminated area E on the sample 14. The occurring fluorescence is collected by the objective lens 13, and reaches the dichroic mirror 6 through the reflecting mirror 12, the secondary objective lens 11, the image rotator 18, the scanner lens 9, the reflecting mirror 8 and the scanning unit 7. The fluorescence concerned is reflected by the dichroic mirror 6, and forms an image of the illuminated area E through the collecting lens 15. Since the illuminated area E is spatially modulated, the image thereof is a modulated image containing modulated components of respective orders. This modulated image is detected by the one-dimensional light detector 16 disposed at a position conjugated with the illuminated area E. Most of extra light beams from portions other than the specimen plane of the sample 14 are cut by the one-dimensional light detector 16 disposed at the position concerned, and thus a confocal effect can be obtained with respect to the short-side direction of the illuminated area E. According to the confocal effect, even when the actual contrast of the structure illumination is low, the contrast of the structure illumination can be essentially increased when the brightness distribution data of the modulated image generated by the one-dimensional light detector 16 are handled.

The brightness distribution data of the modulated image generated by the one-dimensional light detector 16 are transmitted to the data-processing unit 17. The data-processing unit 17 processes the brightness distribution data to obtain a super-resolved image of the sample 14, and displays these data on an image display unit (not shown).

In addition to the above processing, the data-processing unit 17 controls the driving of each part of the microscopic apparatus to obtain necessary information. When the data-processing unit 17 drives the scanning unit 7, the illuminated area E is moved in the short-side direction thereof, and thus the surface of the sample 14 can be scanned by the illuminated area E. Furthermore, when the actuator 19 is driven, the phase of the structured illumination of the illuminated area E (the phase of the spatial modulation) is varied. When the image rotator 18 is driven, the direction of the illuminated area E of the sample 14 can be rotated.

The image rotator 18 is disposed to be nearer to the sample 14 side than the grating 4 and the scanning unit 7. Accordingly, when the direction of the illuminated area E is rotated, the structuring direction Db and the scanning direction Da rotate together. Accordingly, the structuring direction Db and the scanning direction Da for the illuminated area E are unvaried.

Next, the steps associated with the control of the data-processing unit 17 will be described in detail.

FIG. 3 is a flowchart showing an operation associated with the control of the data-processing unit 17. As shown in FIG. 3, the data-processing unit 17 repetitively drives the one-dimensional light detector while scanning the sample 14 with the illuminated area E, thereby obtaining plural brightness data, and then combines these brightness data with one another to obtain image data of a two-dimensional modulated image of the sample 14 (S11). Image data described below are data obtained by scanning the illuminated area E and combining the brightness data.

The data-processing unit 17 further carries out the obtainment of the image data of the modulated image (S11) at plural times while changing the phase of the structured illumination (the loop of S11 to S13). For example, the data-processing unit 17 obtains image data of N (N≧3) while changing the phase every $2\pi/N$.

The image data of the modulated images of N thus obtained are represented by $I_{1j}$ (phase number, j=1, 2, . . . , N), and they are shown in FIG. 4(A). The whole image data $I_{1j}$ (phase number, j=1, 2, . . . , N) of these modulated images contain information for super-resolving in the structuring direction Db (X-direction in FIG. 4).

The data-processing unit 17 carries out the obtainment of the image data of the modulated images of N (the loop of S11 to S13) at plural times (the loop of S11 to S15) while changing the rotating position θ of the illuminated area E and scanning the surface of the sample. For example, the data-processing unit 17 carries out the obtainment of the image data of the modulated images of N totally three times while the rotating position of the illuminated area E is changed every 120°.

The rotating position θ at the time when the image data $I_{1j}$ (j=1, 2, . . . , N) of N shown in FIG. 4(A) are obtained is set to θ=0°, the image data of the modulated images of N obtained under the condition of the rotating position θ=120° are represented by $I_{2j}$ (j=1, 2, . . . , N), and these image data are shown in FIG. 4(B). The image data of the modulated images of N obtained under the condition of the rotating position θ=240° are represented by $I_{3j}$ (j=1, 2, . . . , N), and these image data are shown in FIG. 4(C).

With respect to the image data $I_{1j}$ (j=1, 2, . . . , N) of the modulated images, the image data $I_{2j}$ (j=1, 2, . . . , N) of the modulated images and the image data $I_{3j}$ (j=1, 2, . . . , N) of the modulated images, the rotational positions θ thereof are different from one another every 120°, and thus the structuring directions Db thereof are different from one another every 120°.

Accordingly, the whole of the image data $I_{Mj}$ (M=1, 2, 3, j=1, 2, . . . , N) of the modulated images of 3N contain information for super-resolving in three directions which are different from one another every 120° (M represents the rotating position number).

Next, the steps associated with the processing of the data-processing unit 17 will be described in detail.

FIG. 5 is a flowchart showing an operation associated with the processing of the data-processing unit 17.

(step S21)

The data-processing unit 17 subjects each of the image data $I_{Mj}$ (M=1, 2, 3, j=1, 2, . . . , N) of the modulated images of 3N to Fourier Transformation to obtain image data $I_{kMj}$ (M=1, 2, 3, j=1, 2, . . . , N) of the modulated images of 3N represented in the wave number space. A suffix "k" indicating the coordinate k on the wave number space is attached to the data presented in the wave number space.

(step S22)

The data-processing unit 17 conducts predetermined processing on the image data $I_{k1j}$ (j=1, 2, 3 . . . , N) of the modulated images of M=1 obtained under the condition of the rotating position θ=0° to extract modulated components $I_{kL}$ (L represents the order, and L=+1, 0, −1) of respective orders which are commonly contained in the image data of the modulated images, and the ±1st-order modulated components are displaced and rearranged in the structuring direction Db by only the spatial frequency K of the structured illumination with respect to the 0th-order modulated component to obtain image data $I_{k1}$ of a demodulated images of the sample 14. In FIG. 6, the size of a circle representing the data range of each modulated component $I_{kL}$ (L=+1, 0, −1) corresponds to the resolving limit when no structured illumination is carried out. Furthermore, the $k_x$ axis and $k_y$ axis correspond to the X-axis and the Y-axis in the real space shown in FIG. 4.

Furthermore, the data-processing unit 17 conducts predetermined processing on the image data $I_{k2j}$ (j=1, 2, 3, . . . , N) of the modulated images of M=2 obtained under the condition of the rotating position θ=120° to extract modulated components $I_{kL}$ (L=+1, 0, −1) of the respective orders which are commonly contained in the image data of the modulated images, and these image data are displaced and rearranged in the structuring direction Db by only the spatial frequency K of the structured illumination as shown in FIG. 6(B), thereby obtaining the image data $I_{k2}$ of a demodulated image of the sample 14.

Still furthermore, the data-processing unit 17 conducts predetermined processing on the image data $I_{k3j}$ (j=1, 2, 3, . . . , N) of the modulated images of M=3 obtained under the condition of the rotating position θ=240° to extract modulated components $I_{kL}$ (L=+1, 0, −1) of the respective orders which are commonly contained in the image data of the modulated images, and these image data are displaced and rearranged in the structuring direction Db by only the spatial frequency K of the structured illumination as shown in FIG. 6(C), thereby obtaining the image data $I_{k3}$ of a demodulated image of the sample 14.

An equation represented by the equation (1) may be applied in the processing of this step.

[Equation 1]

$$I_{kj}(k) = \sum_L m_L \exp(2\pi i j/N) O_k(k+LK) P_k(k) \tag{1}$$

However, $O_k(k+LK)P_k(k)$ corresponds to $I_{kL}$, and $m_L$ represents the diffracted intensity of the Lth-order modulated component $I_{kL}$. Note that $O_k(k)$ represents the actual pattern of the sample 14 which is represented in the wave number space, and $P_k(k)$ represents a transfer function of the microscopic optical system from the sample 14 to the one-dimensional light detector 16.

Particularly, for N>3, the least squares method represented by the equation (2) may be applied in the processing of this step. According to the least squares method, the effect of noises superposed on the plural data can be suppressed.

[Equation 2]

$$\begin{bmatrix} \sum_j b_{-1j} I_{kj}(k) \\ \sum_j b_{0j} I_{kj}(k) \\ \sum_j b_{+1j} I_{kj}(k) \end{bmatrix} = \tag{2}$$

-continued $$\begin{bmatrix} \sum_j b_{-1j}^2 & \sum_j b_{-1j}b_{0j} & \sum_j b_{-1j}b_{+1j} \\ \sum_j b_{0j}b_{-1j} & \sum_j b_{0j}^2 & \sum_j b_{0j}b_{+1j} \\ \sum_j b_{+1j}b_{-1j} & \sum_j b_{+1j}b_{0j} & \sum_j b_{+1j}^2 \end{bmatrix} \begin{bmatrix} O_k(k-K)P_k(k) \\ O_k(k)P_k(k) \\ O_k(k+K)P_k(k) \end{bmatrix}$$

However, $b_{Lj}=m_L\exp(2\pi ij/N)$.

(step S23)

The data-processing unit 17 combines the image data $I_{kM}$ (M=1, 2, 3) of three demodulated images shown in FIG. 6 with one another as shown in FIG. 7 to obtain image data $I_k$ of one demodulated image. The 0th-order modulated components $I_{k0}$ contained in the respective image data $I_{kM}$ (M=1, 2, 3) of the three demodulated images represent a common quantity, and thus if the image data $I_{kM}$ (M=1, 2, 3) of the three demodulated images are combined with one another on the basis of the 0th-order modulated component $I_{k0}$, the combination precision can be enhanced.

(step S24)

The data-processing unit 17 subjects the image data $I_k$ of the demodulated image to inverse Fourier Transformation to obtain the image data I of a demodulated image represented in the real space. The image data I of this demodulated image represents a super-resolved image of the sample 14 over the three directions which are different from one another every 120°. This super-resolved image is displayed on the image-displaying unit (not shown) (step S24).

Summarizing the foregoing description, the microscopic apparatus of this embodiment is designed so that the sample 14 is subjected to structured illumination over the predetermined direction (Db) and also a confocal effect can be obtained with respect to the unstructuring direction (Da). The essential contrast of the structured illumination can be enhanced by the confocal effect. Accordingly, the SN ratio of each of the image data $I_{Mj}$ (M=1, 2, 3, j=1, 2, . . . , N) of the modulated images is enhanced, whereby the super-resolved image of the sample 14 is obtained with higher precision.

Furthermore, in the microscopic apparatus of this embodiment, the illumination light is shaped in the form of a line to obtain the confocal effect. Therefore, the information obtainable at a time is limited to one-dimensional information of the sample 14. However, the mechanism for scanning the surface of the sample 14 with the illuminated area E (the scanning unit 7) and the control unit for properly controlling the mechanism concerned and the one-dimensional light detector 16 (the data-processing unit 17) are provided, so that the image data of the two-dimensional modulated image of the sample 14 can be surely obtained.

Still furthermore, the microscopic apparatus of this embodiment is equipped with the mechanism for changing the phase of the structured illumination (the actuator 19) and the control unit for properly controlling the mechanism concerned and the one-dimensional light detector 16 (the data-processing unit 17), so that information for surely obtaining the image data of the demodulated image (the image data of plural modulated images different in phase) can be obtained.

Furthermore, the microscopic apparatus of this embodiment is equipped with the mechanism for changing the structuring direction Db (the image rotator 18) and the control unit for properly controlling the image rotator 18 and the one-dimensional light detector 16 (the data-processing unit 17), so that the direction of the super-resolving can be surely complicated.

(Others)

In this embodiment, the image rotator 18 for rotating the direction of light is used to change the rotating position of the illuminated area E. However, a rotating stage for rotating the arrangement direction of the sample 14 may be used. However, the image rotator 18 is preferably used because it enhances the reproducibility of the rotating position.

Furthermore, in this embodiment, the direction of the super-resolving is set to three directions which are different every 120°. However, the number and type of the directions may be changed. When the direction is limited to one direction, the image rotator 18 may be omitted.

In this embodiment, the demodulating operation for obtaining the demodulated image from the modulated image is carried out in the wave number space (see FIG. 5). However, the demodulating operation may be carried out in the real space as disclosed in Japanese Unexamined Patent Application Publication No. 11-242189. In the demodulating operation of the Japanese Unexamined Patent Application Publication No. 11-242189, image data of three modulated images different in phase are applied to a linear equation. This linear equation corresponds to an equation obtained by representing the equation (1) described above in the real space.

In this embodiment, all the steps for obtaining necessary data are automated (see FIG. 3). However, some of the steps may be manually executed.

Furthermore, in this embodiment, all the steps of processing the obtained data are automated (see FIG. 5), however, some or all of the steps may be manually executed.

The many features and advantages of the embodiments are apparent from the detailed specification and, thus, it is intended by the appended claims to cover all such features and advantages of the embodiments that fall within the true spirit and scope thereof. Further, since numerous modifications and changes will readily occur to those skilled in the art, it is not desired to limit the inventive embodiments to the exact construction and operation illustrated and described, and accordingly all suitable modifications and equivalents may be resorted to, falling within the scope thereof.

The invention claimed is:

1. A microscopic apparatus comprising:
   an illuminating optical system that illuminates a specimen plane of a sample with a line-shaped illuminating light;
   a modulating unit that spatially modulates said illuminating light in a lengthwise direction;
   an image-forming optical system that forms an image of light from said specimen plane illuminated with said spatially modulated illuminating light;
   a detector that detects light from said specimen plane;
   a mechanism that changes the phase of the spatial modulation; and
   a processing part that extracts modulated components of respective orders and obtains demodulated image data by displacing and rearranging the modulated components by a displacement amount equivalent to a spatial frequency of the spatial modulation in wave number space, the modulated components being commonly contained in plural detection signals different in phase.

2. The microscopic apparatus according to claim 1, further comprising a mechanism that rotates said illuminating light relatively to said specimen plane.

3. The microscopic apparatus according to claim 2, further comprising a control unit that obtains a detection signal from said detector at plural times while driving said mechanism.

4. The microscopic apparatus according to claim 2, further comprising a mechanism that scans said specimen plane with said illuminating light.

5. The microscopic apparatus according to claim 1, further comprising a mechanism that scans said specimen plane with said illuminating light.

6. The microscopic apparatus according to claim 5, further comprising a control unit that obtains a detection signal from said detector at plural times while driving said mechanism.

7. The microscopic apparatus according to claim 1, further comprising a control unit that obtains a detection signal from said detector at plural times while driving said mechanism.

8. An observing method comprising:
- a step that illuminates a specimen plane of a sample with line-shaped illuminating light;
- a step that spatially modulates said illuminating light in a lengthwise direction;
- a step that forms an image of light from said specimen plane illuminated with said spatially modulated illuminating light;
- a step that detects light from said specimen plane;
- a step that changes the phase of said spatial modulation; and
- a step that extracts modulated components of respective orders and obtains demodulated image data by displacing and rearranging the modulated components by a displacement amount equivalent to a spatial frequency of the spatial modulation in wave number space, the modulated components being commonly contained in plural detection signals different in phase.

* * * * *